(12) United States Patent
Kostic

(10) Patent No.: US 10,405,784 B2
(45) Date of Patent: Sep. 10, 2019

(54) TISSUE MONITORING APPARATUS AND METHOD

(71) Applicant: Stryker Corporation, Kalamazoo, MI (US)

(72) Inventor: Marko N. Kostic, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 380 days.

(21) Appl. No.: 15/185,347

(22) Filed: Jun. 17, 2016

(65) Prior Publication Data

US 2016/0296150 A1 Oct. 13, 2016

Related U.S. Application Data

(63) Continuation-in-part of application No. 14/708,383, filed on May 11, 2015.
(Continued)

(51) Int. Cl.
*A61B 5/1455* (2006.01)
*A61B 5/1459* (2006.01)
(Continued)

(52) U.S. Cl.
CPC .......... *A61B 5/14553* (2013.01); *A61B 1/227* (2013.01); *A61B 5/0075* (2013.01);
(Continued)

(58) Field of Classification Search
None
See application file for complete search history.

(56) References Cited

U.S. PATENT DOCUMENTS 4,223,680 A * 9/1980 Jobsis .................. A61B 5/0059
600/324
5,666,952 A * 9/1997 Fuse .................. A61B 5/02416
600/310
(Continued)

FOREIGN PATENT DOCUMENTS

EP 0443267 A1 8/1991
EP 2725507 B1 4/2014
(Continued)

OTHER PUBLICATIONS

Machine translation of JP2004-129809A.*
(Continued)

*Primary Examiner* — Michael R Bloch
(74) *Attorney, Agent, or Firm* — Warner Norcross + Judd LLP

(57) ABSTRACT

A tissue monitoring device includes a light emitter, a light detector, a probe, and a controller. The light emitter emits light through tissue in the subject, such as tissues in the subject's head. The light detector detects light emitted from the light emitter and scattered by the subject's tissue. The probe is inserted into an orifice of the subject and includes one of the light emitter and light detector. The controller communicates with the light detector and the light emitter and detects an oxygenation level of the blood in the subject's tissue based upon measurements of the scattered light. The probe may include one or more bladders for blocking ambient light and/or for ensuring contact exists between the light detector (or emitter) and an interior surface of the subject's orifice.

11 Claims, 11 Drawing Sheets

Related U.S. Application Data

(60) Provisional application No. 61/993,099, filed on May 14, 2014.

(51) Int. Cl.
   *A61B 1/227* (2006.01)
   *A61B 5/00* (2006.01)
   *A61B 5/0205* (2006.01)
   *A61B 5/026* (2006.01)
   *A61F 7/00* (2006.01)
   *A61B 5/024* (2006.01)

(52) U.S. Cl.
   CPC ........ *A61B 5/02055* (2013.01); *A61B 5/0261* (2013.01); *A61B 5/1459* (2013.01); *A61B 5/14552* (2013.01); *A61B 5/4848* (2013.01); *A61B 5/02416* (2013.01); *A61B 5/6817* (2013.01); *A61B 5/6853* (2013.01); *A61B 2562/0238* (2013.01); *A61B 2562/0247* (2013.01); *A61B 2562/185* (2013.01); *A61F 7/00* (2013.01); *A61M 2230/00* (2013.01)

(56) References Cited

U.S. PATENT DOCUMENTS

| | | | |
|---|---|---|---|
| 6,078,829 A * | 6/2000 | Uchida | A61B 5/02427 600/310 |
| 6,280,390 B1 | 8/2001 | Akselrod et al. | |
| 6,353,226 B1 * | 3/2002 | Khalil | A61B 5/14532 250/339.11 |
| 6,577,884 B1 | 6/2003 | Boas | |
| 7,544,168 B2 | 6/2009 | Nitzan | |
| 7,803,120 B2 | 9/2010 | Banet et al. | |
| 8,788,005 B1 | 7/2014 | Cheng | |
| 2004/0024297 A1 * | 2/2004 | Chen | A61B 5/14553 600/323 |
| 2005/0209516 A1 * | 9/2005 | Fraden | A61B 5/02055 600/323 |
| 2009/0069645 A1 * | 3/2009 | Nielsen | A61B 5/02 600/301 |
| 2010/0198029 A1 * | 8/2010 | Wang | A61B 5/14553 600/323 |
| 2011/0118564 A1 | 5/2011 | Sankai | |
| 2011/0263950 A1 | 10/2011 | Larson et al. | |
| 2013/0276785 A1 * | 10/2013 | Melker | A61B 5/14551 128/204.23 |
| 2014/0115784 A1 | 5/2014 | Johannigman et al. | |
| 2014/0165049 A1 | 6/2014 | Diamos et al. | |
| 2015/0105636 A1 | 4/2015 | Hayman et al. | |
| 2017/0319116 A1 * | 11/2017 | Chang | A61B 5/14553 |

FOREIGN PATENT DOCUMENTS

| | | | |
|---|---|---|---|
| JP | 2004129809 A * | 4/2004 | |
| WO | 1998034577 A1 | 8/1998 | |
| WO | 2007047667 A2 | 4/2007 | |
| WO | 2011113070 A1 | 9/2011 | |
| WO | 2013001265 A2 | 1/2013 | |
| WO | 2016074648 A1 | 5/2016 | |

OTHER PUBLICATIONS

"Optical investigations of physiology. A study of intrinsic and extrinsic biomedical contrast." Philosophical Transactions of the Royal Society Biological Sciences, 1997.

"Functional Near-InfraRed Imager". University of Pennsylvania, Philadelphia, 1997.

"The Science of Phototherapy: An Introduction" Chapter 5, Tissue Optics, 5.1 Concepts of Tissue Optics, Dec. 5, 2005.

* cited by examiner

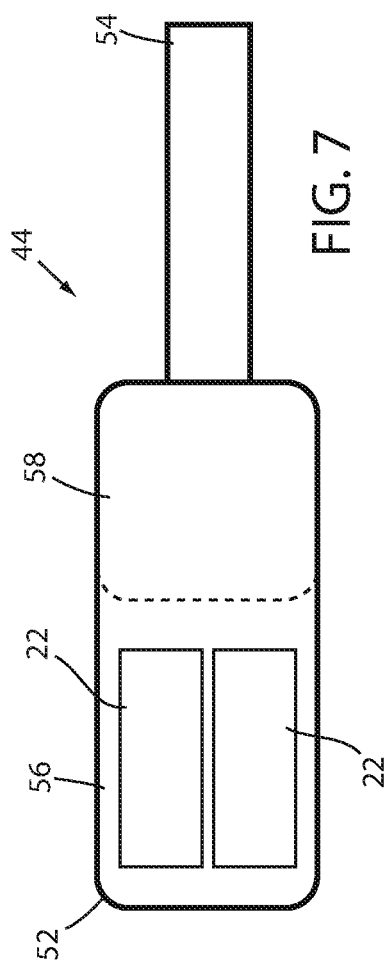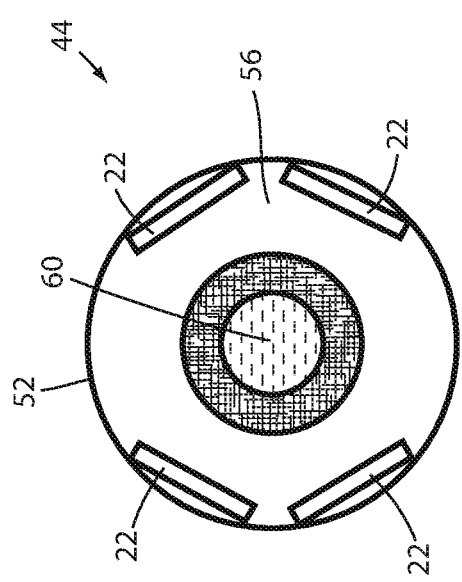

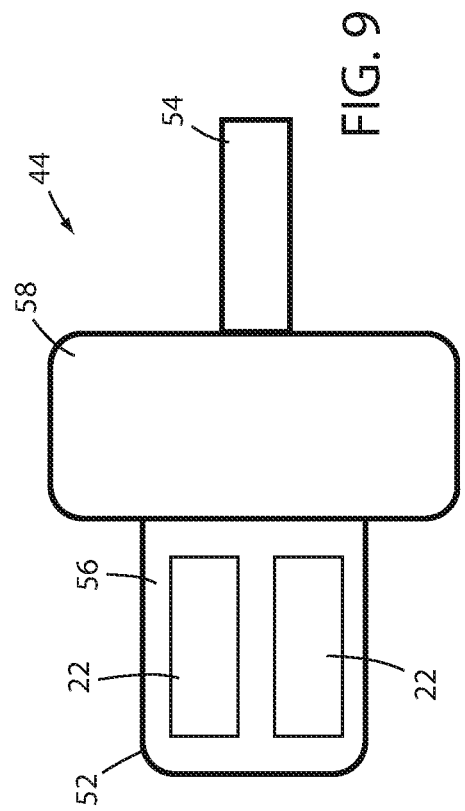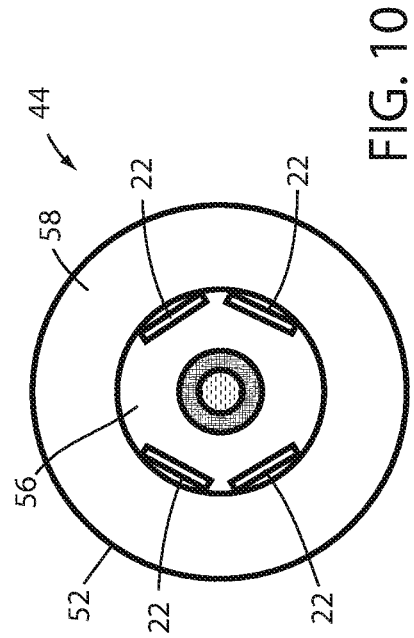

TISSUE MONITORING APPARATUS AND METHOD

This application is a continuation-in-part of U.S. patent application Ser. No. 14/708,383 filed May 11, 2015, by inventors Marko Kostic et al. and entitled TISSUE MONITORING APPARATUS AND SYSTEM, which in turn claims priority to U.S. provisional patent application Ser. No. 61/993,099, filed on May 14, 2014, the complete disclosures of both of which are incorporated herein by reference in their entirety and are commonly owned by Stryker Corporation of Kalamazoo, Mich.

BACKGROUND

The present disclosure relates to monitoring the cerebral tissue of a subject (e.g. person or animal), such as, but not limited to, the oxygenation levels of the tissue, the cytochrome-a levels of the tissue, and/or the water content of the tissue.

SUMMARY

A tissue monitoring apparatus or system is described that is configured to monitor a subject's tissue and to collect data from the tissue, which may be used to determine one or more parameters about the tissue state, for example, changes in tissue perfusion or changes in tissue metabolism, in order to provide information, including feedback information, which may provide a more complete clinical picture about the subject's condition. Such information may include information indicating the potential occurrence of a stroke in the subject, and/or other types of information.

According to one embodiment, an apparatus for monitoring a subject's tissue is provided that includes a light emitter, a light detector, a probe, and a controller. The light emitter emits light through tissue in the subject's head. The light detector detects light emitted from the light emitter and scattered by the tissue of the subject's head. The probe is adapted to be inserted into an orifice of the subject's head and includes the light emitter or the light detector (and possibly more than one of these). The controller communicates with the light detector and light emitter and detects an oxygenation level of blood in the subject's head based upon measurements of the scattered light detected by the light detector.

According to another embodiment, an apparatus for monitoring a subject's tissue is provided that includes a first light emitter, a second light emitter, a light detector, a probe, and a controller. The first and second light emitters emit light through tissue in the subject's head. The light detector detects light emitted from the first and second light emitters and scattered by the tissue of the subject's head. The probe is adapted to be inserted into an orifice of the subject's head and includes either: (1) the first and second light emitters, or (2) the light detector. The controller communicates with the light detector and first and second light emitters and is adapted to synchronize readings taken from the light detector with light emissions emitted by the first and second light emitters to thereby monitor a state of the subject's tissue.

According to still another embodiment, an apparatus for monitoring a subject's tissue is provided. The apparatus includes first and second units, first and second probes, and a controller. The first unit includes first and second light emitters adapted to emit light through a first region of the subject's head. The second unit includes third and fourth light emitters adapted to emit light though a second region of the subject's head. The first probe is adapted to be inserted into a first ear canal of the subject and includes a first light detector adapted to detect light emitted from the first and second light emitters and scattered by the first region of the subject's head. The first probe also includes a first temperature sensor. The second probe is adapted to be inserted into a second ear canal of the subject and includes a second light detector adapted to detect light emitted from the third and fourth light emitters and scattered by the second region of the subject's head. The second probe also includes a second temperature sensor. The controller communicates with the first and second light detectors and detects an oxygenation level of blood in the first region of the subject's head based upon measurements of the scattered light detected by the first light detector. The controller also detects an oxygenation level of blood in the second region of the subject's head based upon measurements of the scattered light detected by the second light detector. Still further, the controller compares temperature readings from the first and second temperature sensors.

According to other aspects, any of the probes may include an inflatable bladder adapted to inflate inside of the subject's orifice and block ambient light from reaching the light detector.

The probe or probes include, in some embodiments, an inflatable bladder adapted to urge the light detector or the light emitter against an interior surface of the orifice when the inflatable bladder is inflated.

In some embodiments, the probe includes a sensor for determining a relative location of the probe within the orifice. The sensor is an image sensor in some of these embodiments. In others of these embodiments, the sensor is a pressure sensor.

The first and second light emitters emit light having first and second wavelengths, respectively, in some embodiments. In some of these embodiments, the first wavelength corresponds to a red light and the second wavelength corresponds to a near infrared light.

The light detector is coupled to the probe in some embodiments and the light emitter is adjustably positionable with respect to the probe such that the light emitter may be placed at different locations on the subject's head while the probe remains in the subject's orifice.

Before the various embodiments disclosed herein are explained in detail, it is to be understood that the claims are not to be limited to the details of operation, construction, and/or arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTIONS OF THE DRAWINGS

FIG. 7 is a side elevation view of a probe of the embodiment of FIG. 6 shown with first and second bladders in deflated states;

FIG. 8 is an end view of the probe of FIG. 7;

FIG. 9 is a side elevation view of the probe of FIG. 7 shown with the first and second bladders in inflated states;

FIG. 10 is an end view of the probe of FIG. 9;

DETAILED DESCRIPTION OF THE EMBODIMENTS

Figure 1:
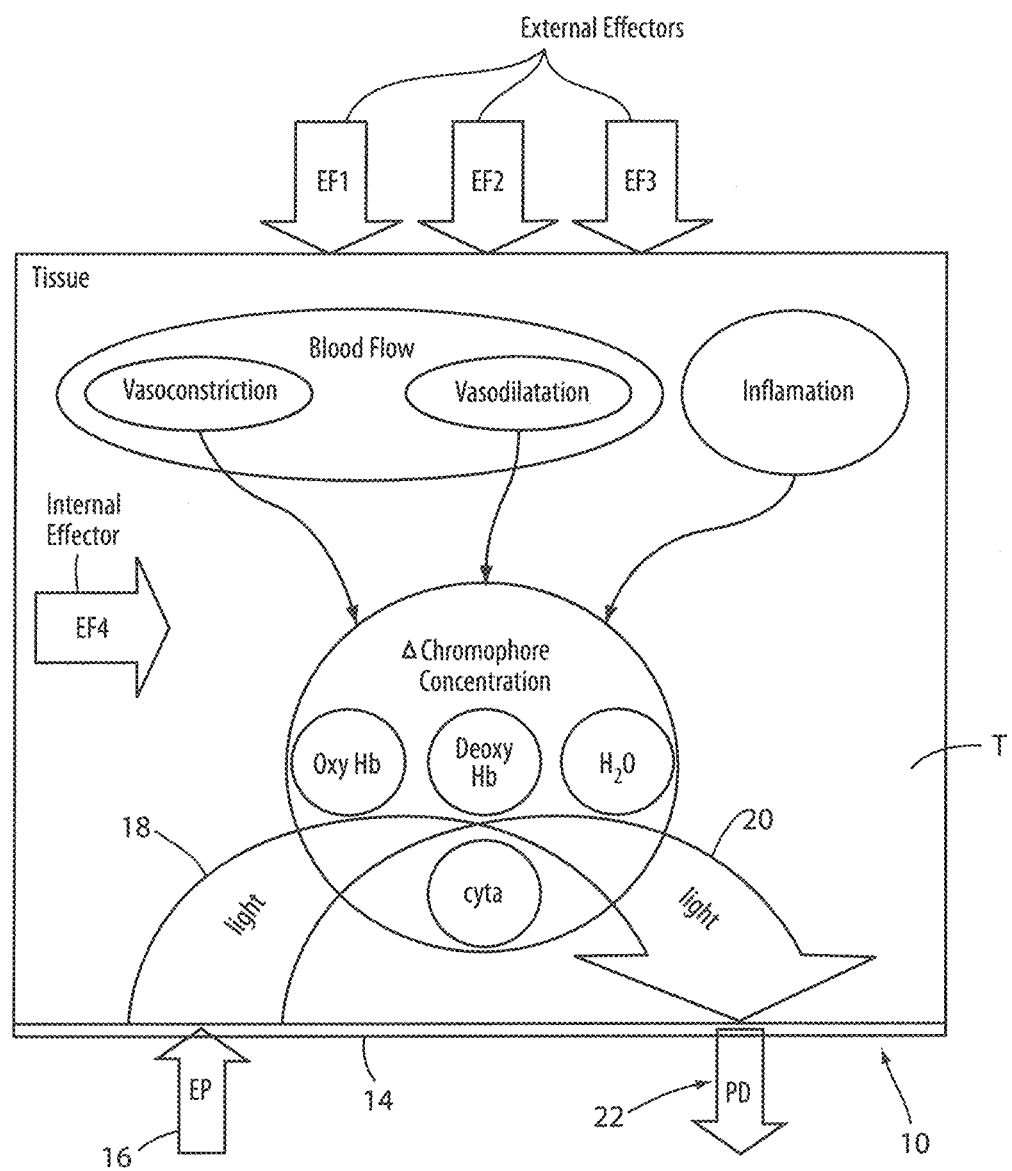
FIG. 1 is a schematic view of a tissue monitoring system.

Referring to FIG. 1, the numeral 10 generally designates an apparatus for monitoring a change or changes in tissue. As will be more fully described below, apparatus 10 is configured to monitor changes in tissue to assess the condition of a person or an animal (i.e. the subject), including the clinical effect of a treatment on a subject. The type of conditions or treatments may vary and include, for example, thermal conditions, brain perfusion, heart conditions, trauma, physical interface, such as pressure, temperature management therapy, drug therapy, wound treatment, or surgery.

Apparatus 10 is configured to measure the tissues response to external and/or internal effecters. External effecters include, for example, temperature, force, and chemicals. Internal effecters include, for example, pharmacological compounds (e.g. drugs), infection, or acts upon the tissue causing specific physiological responses. For example, physiological responses may include tissue responses from positive or negative pressure, which may include vasoconstriction, vasodilation or inflammation. Positive pressure may be applied to when a person is supported on a surface, such as a mattress or a pad. Negative pressure may be applied, for example, when wounds are treated with negative pressure. These physiological responses result in concentration changes of specific tissue chromophores (e.g., oxygenated and deoxygenated hemoglobin, water, cytochrome a). The rate at which these changes occur can provide an indication of the severity of the condition.

For example, the intensity of the inflammation process is usually proportional to the degree of tissue injury. When certain infections occur, inflammation can develop very rapidly. The body's response to inflammation is to enlarge macrophage cells followed by mobilization of the macrophage cells to provide a first line of defense. The second line of defense is the invasion of neutrophil cells. In each case, the migration of such cells provides valuable insight into a condition of a tissue. Similarly, changes in concentration of other tissue chromophores can provide valuable information about the subject's response to treatment.

Figure 2:
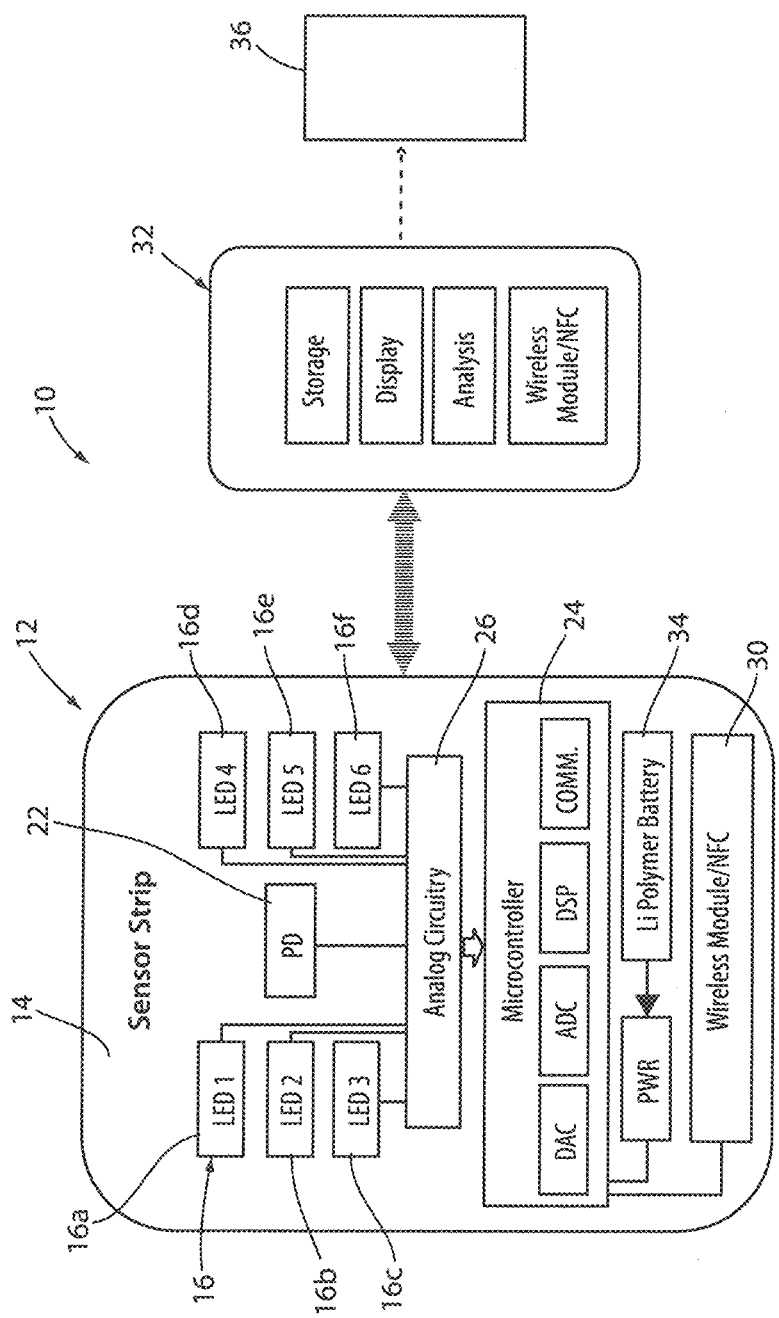
FIG. 2 is a schematic view of a tissue monitoring device applied to tissue.

Referring to FIG. 2, apparatus 10 includes a sensor assembly 12, which is configured to emit and direct light on tissue, including external tissue or internal tissue, including vascular tissue, and to detect the light scattered by the tissue to measure how the chromophore levels at different depths of the tissue vary.

In the illustrated embodiment, sensor assembly 12 is mounted to a carrier 14 and includes a light source 16, which is also mounted on carrier 14. Carrier 14, for example, may comprise a flexible strip of dielectric material with an optional adhesive layer applied thereto, which allows the assembly to be applied to tissue, for example, when applied to external tissue. Further, carrier 14 may be disposable. As will be described below, a variety of different substrates may be used for carrier 14 and other methods of attachment may be used, especially when applied to internal tissue.

Light source 16 emits light at at least one frequency, for example, between 600 and 1400 nm, which is known as a biologically relevant spectrum. As noted above, light source 16 directs light 18 onto a subject's tissue T through the incident surface. The light is then scattered in the tissue by encountering numerous scatterers that will cause a change in its direction. A fraction of photons is scattered such that these photons exit tissue at the incident surface. The concentration of chromophores of interest along the scattering path will affect photon absorption and, therefore, determine the fraction of initially emitted light that is scattered back at the incident surface.

The scattered light 20 (FIG. 1) is then detected by at least one detector 22, such as a photosensor or photodetector, including a photodiode, a phototransistor, a photomultiplier, a photoresistor, an active pixel sensors (APSs), or a charge coupled device (CCD) or the like, which also may be mounted to carrier 14. Detector 22 detects the scattered light that exits the surface of the tissue and may detect a single frequency or multiple frequencies, including a broad spectrum of frequencies.

In the illustrated embodiment, detector 22 is located adjacent but spaced from light source 16 so that detector 22 detects light exiting from the same surface, though spaced from, light source 16. Detector 22 is then coupled (either directly or wirelessly) to a microcontroller 24 via circuitry 26 (either analog or digital), which also may be mounted to carrier 14. Microcontroller 24 includes a processor and memory, which may store suitable software or applications that are executed by the processor to receive the signals from detector 22 and may analyze the signals to evaluate the physiological changes in the underlying tissue, and thereby together with light source 16 and detector 22 form a tissue monitoring device. Microcontroller 24 may include an analog digital converter (ADC) when circuitry 26 is analog. It should be understood that microcontroller 24 may also be remotely mounted, separate and apart from the tissue monitoring device, with detector 22 coupled to microcontroller 24 wirelessly via a transmitter provided in the tissue monitoring device so that detector 22 can transmit information about the scattered light, for example, the scattered light intensity to microcontroller 24.

Physiological changes in the underlying tissue manifest themselves in changes in concentration of specific tissue chromophores, for example, oxygenated and deoxygenated hemoglobin, water, cytochrome a. These concentration changes are detected via attenuation (i.e. absorption) of chromophore-specific wavelengths of light (i.e. photons) that are sourced by the light source 16. Once the acquired signal is processed by microcontroller 24, the information may then be communicated via a communication device 30, for example, a wireless module, such as a Bluetooth device or a near field communication (NFC) device to a remote device 32. Apparatus 10 may, therefore, form part of a feedback loop for a control system of another device, more fully described below.

To power light source 16, detector 22, and microcontroller 24, apparatus 10 may also incorporate a power supply 34, which may also be mounted to carrier 14. Power supply 34 may comprise a capacitor or an electrochemical cell, such as a lithium polymer battery or the like, and corresponding circuitry.

As noted above, sensor assembly 12 includes a light source 16. Light source 16 may comprise one or more discrete light sources. In different configurations, light sources are contiguous or spaced. Further, each light source may generate light at a single frequency, multiple frequencies, or a broad spectrum of frequencies. For example, the light source may comprise a light emitting device, such as an LED, a laser, or a plasma lamp. In the illustrated embodiment, light source 16 comprises six spaced light sources 16a, 16b, 16c, 16d, 16e, and 16f (e.g. LEDs). Optionally, one group of light sources 16a-16c may generate light at one frequency, for example, in the red segment of the light spectrum, and another group of light sources 16d-16f may generate light at a second, different frequency, such as the near infra-red segment of the light spectrum so that chromophores that absorb the red light can be distinguished from the chromophores that absorb the infrared light. For example, a suitable wavelength for one group may be from about 600-700 nm or about 650 nm, and a suitable wavelength for the other group may be from about 850-950 nm or about 900 nm. At these wavelengths, tissue chromophores are major absorbers of photons. The photon absorption attenuates the detected light and, hence, enables extrapolation of information about clinically-relevant intracellular and extracellular elements of the tissue.

By measuring the scattered light intensity and comparing it to the incident light intensity, microcontroller 24 can measure the amount of attenuation of the scattered light to measure the absorption that accrued in the tissue for each frequency of light, which can then be used to determine the concentrations of chromophores of interest to determine, for example, the oxygenated or deoxygenated hemoglobin, water, or cytochrome a. This information, when monitored continuously or periodically, can then be used by the microcontroller 24 to identify trends in the subject's relative physiological condition, for example, a physiological condition related to disease, illness, injury, or a subject's response to treatment.

Further, as briefly noted above, this information may be forwarded to remote device 32 for storage, display, for example, to a caregiver, further analysis, or for controlling a second remote device, for example, such as a treatment device 36. For example, treatment device 36 may comprise a temperature management device for applying thermal therapy to a subject. Suitable temperature management devices, such as warming devices or cooling devices, are available from Stryker Corporation under the trademark Medi-Therm®. Thermal management systems, such as a Medi-Therm® device from Stryker, may be used by a caregiver in situations where a patient's own body is unable to adequately control core temperature due to certain factors, such as disease, injury, anesthesia, open cavity surgery. Thus, apparatus 10 may provide input to the temperature management device to control the temperature and duration of the applied temperature based on the real-time feedback information determined by microcontroller 24.

The human body contains many cold and warmth receptors found primarily in the skin, spinal cord, abdominal viscera, and thorax. These receptors are responsible for providing temperature information from the body to hypothalamus and its numerous temperature-regulating centers. The main role of these temperature regulating centers is to detect abnormal body temperatures and to initiate body's response to either increase or decrease a body's temperature. In healthy individuals, there are three primary mechanisms that decrease body's temperature and three opposite mechanisms that increase body's temperature. The three mechanisms for decreasing temperature include: (1) Vasodilation of skin blood vessels, which results in increased blood flow, (2) sweating, and (3) decrease in body's heat production through inhibition of shivering and chemical thermogenesis, including the slowing of metabolic processes. In contrast, the body increases temperature through: (1) Vasoconstriction, which results in a decrease of blood flow, (2) piloerection, and (3) increase in chemical thermogenesis.

Based on the fact that primary temperature control mechanisms involve increase and decrease of blood flow, blood flow is, therefore, also a factor when evaluating a subject's response to temperature changes. Poiseuille's Law states that the fluid flow is proportional to the fourth power of the vessel radius. This means that very small changes in blood vessel radius will have profound effect on the blood flow though that vessel. Changes in blood flow, due to vasoconstriction or vasodilatation, will result in a change of delivered oxygenated hemoglobin and removed deoxygenated hemoglobin from the tissue. These oxy- and deoxy-hemoglobin changes may be detected using a near infrared spectroscopy system.

Figure 2A:
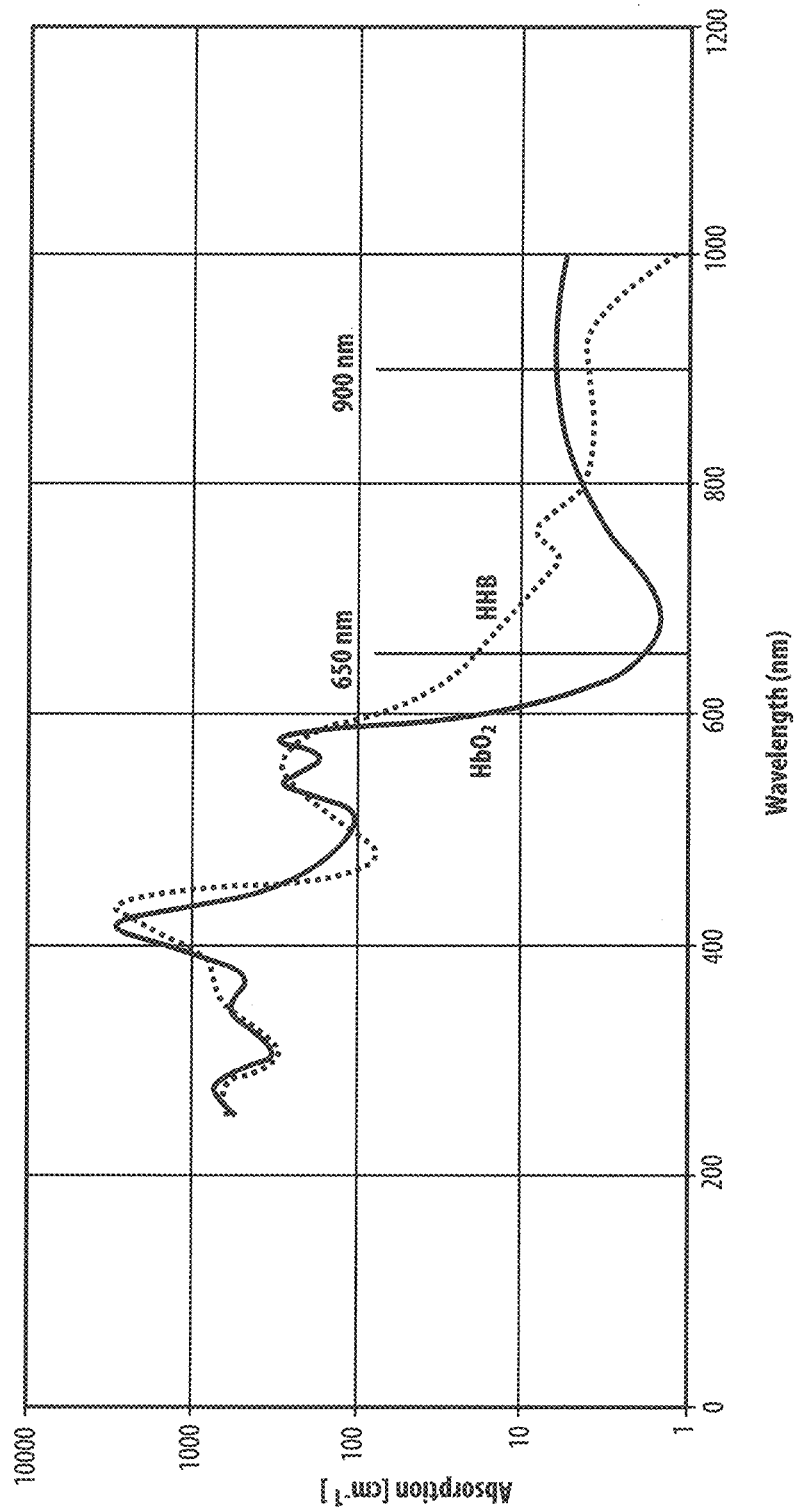
FIG. 2A is a graph illustrating the Absorption Spectra of Oxygenated (HbO2) and Deoxygenated (HHb) Hemoglobin.

Near infrared spectroscopy systems exploit tissue scattering and absorption of visible and near-infrared light (hence near infrared spectroscopy, NIRS) to detect changes in oxygenated and deoxygenated hemoglobin levels at various tissue depths. The detection of changes in hemoglobin is accomplished using light sources with at least two different wavelengths (e.g., 650 nm and 900 nm). At these wavelengths, tissue chromophores are major absorbers of photons. (FIG. 2A). For example, increased concentration of oxygenated hemoglobin results in increased number of chromophores in tissue, which reduce the number of photons (at 900 nm wavelength) being detected on the surface of the tissue. Dependence (1) shows this inverse relationship between the concentration of chromophores in tissue and a number of detected photons on the tissue surface.

$$C_\lambda \propto \frac{1}{n_\lambda} \qquad (1)$$

Based on the physiological temperature control mechanism of the human body and the detection capabilities of the NIRS system, the following are expected responses to thermal management therapy:

TABLE 1

Expected Physiological and NIRS System Responses to Thermal Management

| Therapy | Body Response | | | NIRS System Response (number of detected photons) | |
| --- | --- | --- | --- | --- | --- |
| | Blood Vessels | Oxy Hemoglobin Concentration | Deoxy Hemoglobin Concentration | 650 nm (deoxy) | 900 nm (oxy) |
| Cooling | Vasoconstriction | ↓ | Initially ↓ then possibly ↑ | Initially ↑ then possibly ↓ | ↑ |
| Warming | Vasodilatation | ↑ | ↑ | ↓ | ↓ |

Therapy

Table 1 shows that during the course of applying thermal therapy, such as a cooling thermal management therapy, blood vessels will constrict and cause a reduction in blood flow to monitored tissue. The reduction in blood flow to the tissue will cause a decrease in oxygenated hemoglobin concentrations resulting in detection of increased number of photons in the 900 nm region (dependence 1, above and FIG. 2A). In contrast, during warming thermal therapy, blood vessels will dilate causing an increase in blood flow to the monitored tissue, which will cause an increase in oxygenated hemoglobin concentrations resulting in detection of fewer numbers of photons in the 900 nm region. Therefore, based on the detection of photons in these regions, the microcontroller 24 can determine when continued treatment, cessation of treatment or a change in temperature is indicated, which can then be used to control the temperature management device.

Other remote devices that may be controlled by apparatus 10 include a support surface, for example, a medical mattress that provides medical treatment. Medical mattresses are often constructed as dynamic mattresses (e.g. mattresses with pneumatic bladders or fluidized beds) that can be adjusted to redistribute pressure to reduce the risk of a patient forming a pressure ulcer. In some cases, medical mattresses or toppers may have percussion or vibration devices that apply forces to the patient to help break-up the phlegm, for example, in patient's lungs. Other mattresses or toppers may incorporate stimulation devices, such as described in commonly assigned U.S. Pat. No. 8,480,573 issued to Neustaedter et al. and entitled APPARATUSES FOR AND METHOD OF PREVENTING DECUBITUS ULCERS, the complete disclosure of which is hereby incorporated herein by reference. Apparatus 10, therefore, may be coupled to the control system of a mattress or topper and provide input to the control system to provide an indication, for example, when a patient may need to be turned, receive percussion or vibration treatment or be stimulated to be moved. For example, the signals received by detector 22 may be analyzed to determine the level of oxygenation in the capillary bed of soft tissue, which can be indicative of the development of a pressure ulcer. Apparatus 10 may also include other sensors, such as a sensor to detect moisture and/or a sensor to detect temperature, which when combined with the oxygenation level information may provide a predictor of whether a subject is at risk of developing a pressure ulcer. When such risk is determined, then apparatus 10 may provide signals to the mattress control system to indicate that the patient should be turned, for example. Alternately or in addition, apparatus 10 may generate an alarm, such as a local alarm at the bed or an alarm through the bed communication system so that an alarm is sent to a nurse call system, for example. In addition, as noted, apparatus 10 may include a display, which is configured to display a map of the patient's interface with the mattress or topper that indicates regions where the risk of developing a pressure ulcer is elevated, for example, based on the oxygenation level information and other optional parameters (e.g., temperature and/or moisture).

Other remote devices that may receive input from apparatus 10 include reduced pressure therapy devices, such as vacuum assist devices (VACs), which are used in wound healing. A caregiver typically secures a VAC device to a subject's tissue around a wound, which applies a reduced pressure or vacuum to the wound, for one or multiple treatments until the wound is closed or at least partially closed. It has been shown that providing a vacuum or reduced pressure in proximity to a wound site accelerates the growth of new tissue at the wound. The negative pressure treatment increases capillary blood flow to the area and consequently faster formulation of granulation in the underlying tissue. Current dressings, however, can lead to maceration of the region around the wound. By monitoring the subject's tissue response to the negative pressure treatment, the negative pressure treatment may be adjusted automatically either in duration or pressure based on how the subject is responding. For example, apparatus 10 may be used to monitor the increased blood flow in the vicinity of the wound, inflammation, or to monitor granulation tissue formation to provide a measure of how the wound healing process is progressing or whether a VAC device is needed. The classic model of wound healing comprises three overlapping phases: inflammation, proliferation and remodeling. Within the first few minutes after the injury, a clot is formed, which reduces active bleeding. During the inflammation phase, bacteria and cell debris are removed from the wound by white blood cells. Blood factors are released into the wound that cause the migration and division of cells during the proliferative phase. The proliferation phase is characterized by angiogenesis, collagen deposition, granulation tissue formation, epithelialization, and wound contraction. By detecting that a wound is progressing normally, a clinician may decide that negative pressure treatment is not needed. On the other hand, the information collected by apparatus 10 may indicate negative pressure treatment is suitable and, further, as noted may provide feedback to the VAC device based on the patient's tissue response to treatment. For example, if during treatment, apparatus 10 detects that there is an increased blood flow to the monitored tissue area, apparatus 10 may provide input to the VAC device to terminate, continue treatment or adjust the pressure or may initiate an alarm to a caregiver to indicate to the caregiver that the VAC device should be turned off.

Further, in each case apparatus 10 may be incorporated into the treatment device itself to form part of a control feedback loop for the treatment device or may be simply in communication with the device either by hardwiring or wireless transmission or in communication with a caregiver through the display or through an alarm.

Figure 3:
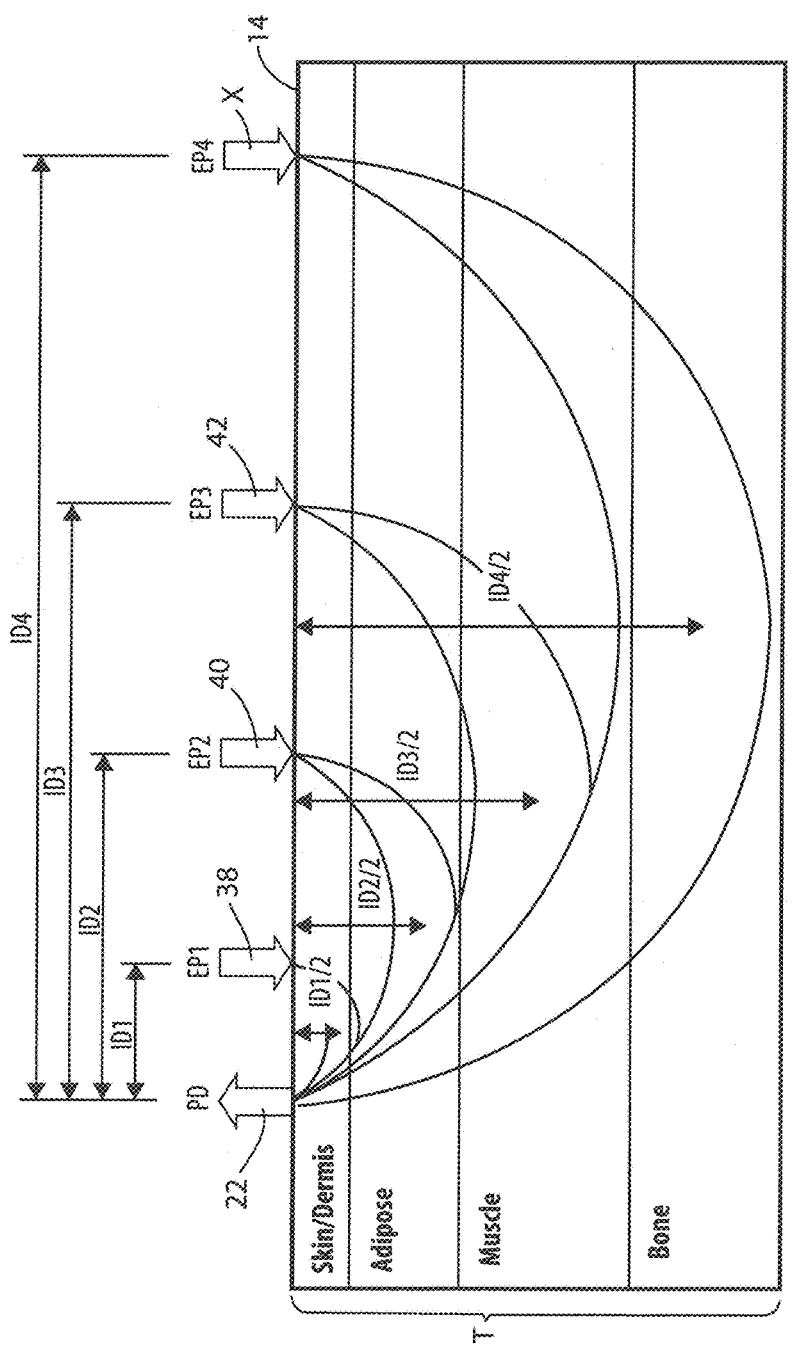
FIG. 3 is an illustration of the operation of the tissue monitoring device.

As described above, light source 16 may be supported on carrier 14, which may be adapted to be applied to a subject's tissue, such as skin. Further, as described above, light source 16 may have multiple light sources (16*a*-16*f*). Referring to FIG. 3, the light sources may be arranged in pairs 38 (e.g. 16*a* and 16*d*), 40 (e.g. 16*b* and 16*e*), 42 (e.g. 16*c* and 16*f*), and X. Each pair includes one light source emitting light at one frequency and the other light source emitting light at a second frequency different than the first frequency. For example, as noted, one frequency could fall in the red region of the light spectrum, and the other in the near infrared range of the light spectrum. Each pair 38, 40, 42 . . . X is spaced from detector 22 so that their incident light samples different tissue depth. As best seen in FIG. 3, the further the spacing the greater the depth of tissue sampled. Thus, apparatus 10 can be used to measure how chromophore levels vary in different tissue layers. The inter-optode distance ($ID_1$, . . . $ID_4$), between detector 22 and the light source pair determines the sampling depth. As noted, the distance between the light source(s) and the detector(s) determines extent of light penetration into the tissue and can extend up to about 3 cm in depth.

As noted above, carrier 14 may be formed from a flexible substrate with an adhesive backing or layer so that sensor assembly 12 may be placed on the subject's tissue and retained in place by the adhesive. Alternately, a strap or other holding device may be used to keep sensor assembly 12 in place. Further, carrier 14 may comprise a flexible substrate in the form of a film or transfer sheet so that the sensor assembly 12 may be transferred onto tissue and then left in place without the carrier.

Figure 4:
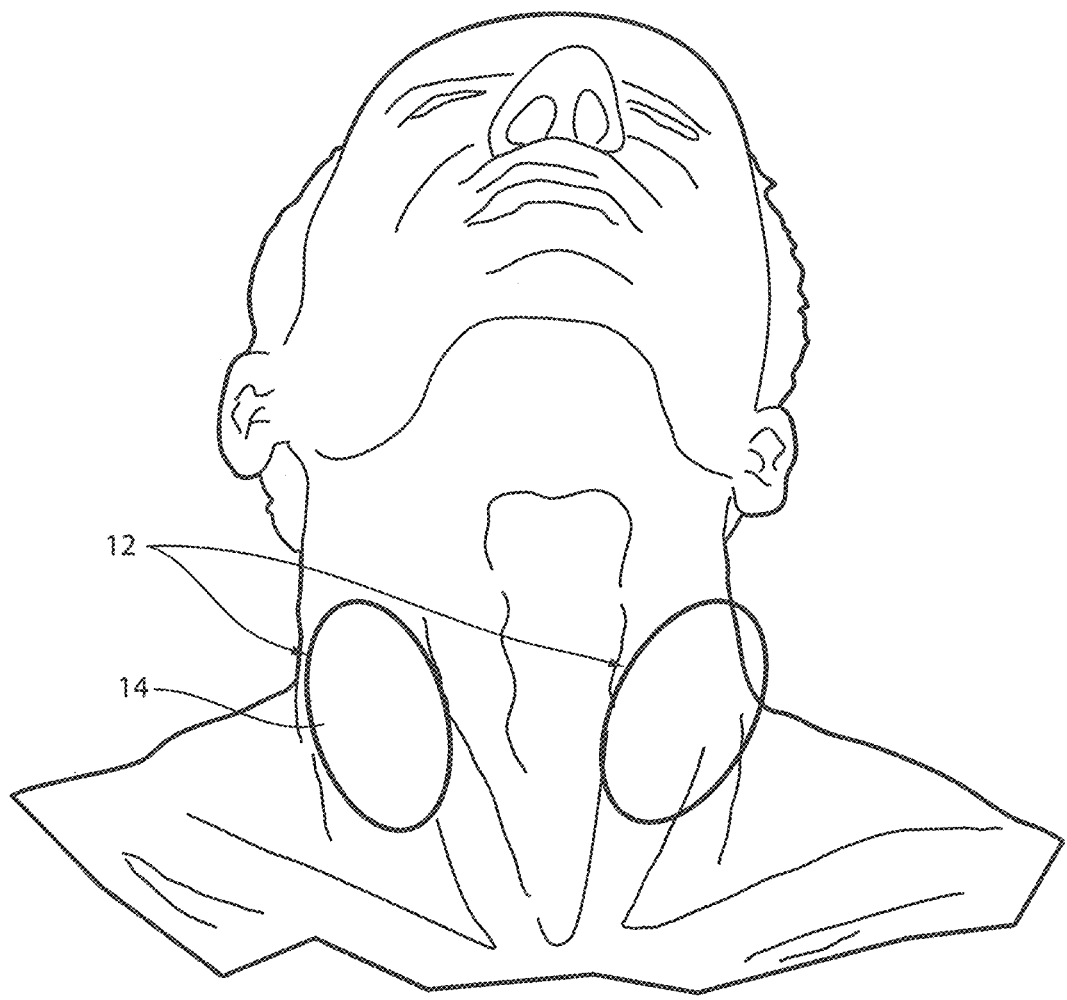
FIG. 4 is an illustration of the tissue monitoring device located on a person's neck.
Figure 5:
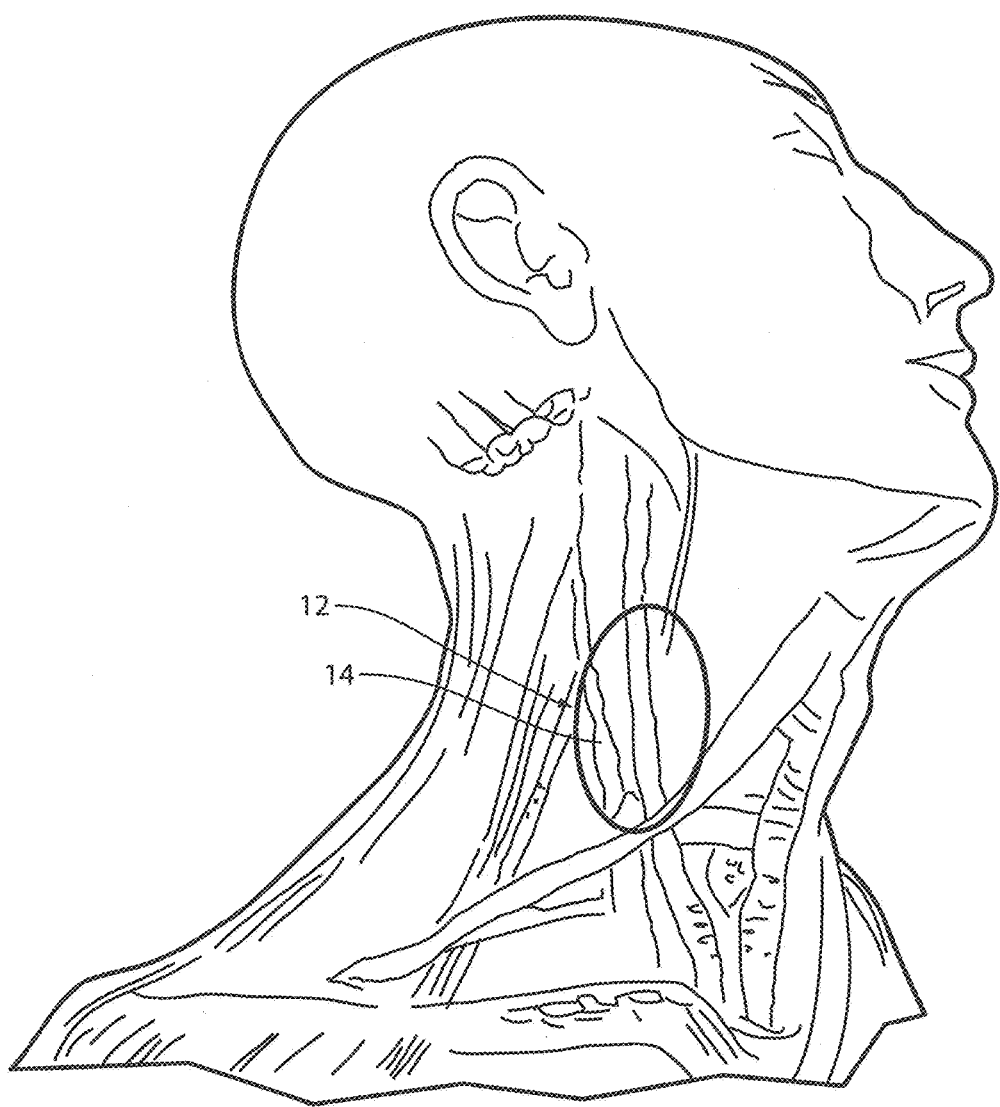
FIG. 5 is an illustration of the underlying vasculature that may be located underneath the tissue monitoring device when located on a person's neck.

The location of sensor assembly 12 may vary. For example, referring to FIG. 4, sensor assembly 12 may be located on a subject's neck to detect changes in oxygenated and deoxygenated blood flowing from the heart to the brain or from the brain to the heart and lungs. Referring to FIG. 5, sensor assembly 12 may be applied to the skin and located over the common carotid artery (right side shown, but can also be applied to left side) to detect changes in oxygenated blood flowing from the heart to the brain. A second sensor assembly may be placed over the left side to monitor both left and right vascular structures. The assembly may also be placed over external and internal veins (e.g. internal jugular vein and external jugular vein) again to detect changes in deoxygenated blood flow from the brain to the heart and lungs. When several sensor assemblies are used, they may operate independently or they may be in communication with each other and have a shared microcontroller or may send signals to a central microcontroller, which processes the signals from the microcontrollers of all sensor assemblies.

Sensor assembly 12 may also be placed internally in a subject's body. For example, carrier 14 and/or sensor assembly 12 may be mounted to a stent, or carrier 14 may be configured as a stent. Similarly, carrier 14 and/or sensor assembly 12 may be mounted to a catheter. In this manner, tissue monitoring apparatus 10 may be used to monitor activity in a vascular structure, for example to monitor brain perfusion or to monitor other organs such as the heart, kidneys, lungs, or liver.

Thus, a tissue monitoring device and method are described that provide a non-invasive, lower power device and/or method for detecting changes in tissue state, for example, changes in tissue oxygenation levels, either as a result or internal factors or external factors, including treatment. The device and/or method can provide depth dependent information about a subject's tissue, which may be used to determine various parameters about the tissue state, including changes in perfusion and changes in the underlying tissue metabolism as it relates to these external and/or internal factors. This physiological information can be displayed or relayed or used to provide feedback information for the control of a remote device, such a treatment device, including a medical mattress.

As described, the present tissue monitoring device may consist of two components, a sensor assembly and a carrier, such as a disposable sensor strip. The sensor assembly may have one or more light sources and one or more detectors. The device may include a microcontroller and a wireless module for data transmission—or may be directly coupled to another device, such as a display or treatment device. It should be understood that alterations and changes can be made without departing from the spirit and broader aspects of the invention as defined in the appended claims, which are to be interpreted in accordance with the principles of patent law including the doctrine of equivalents.

Figure 6:
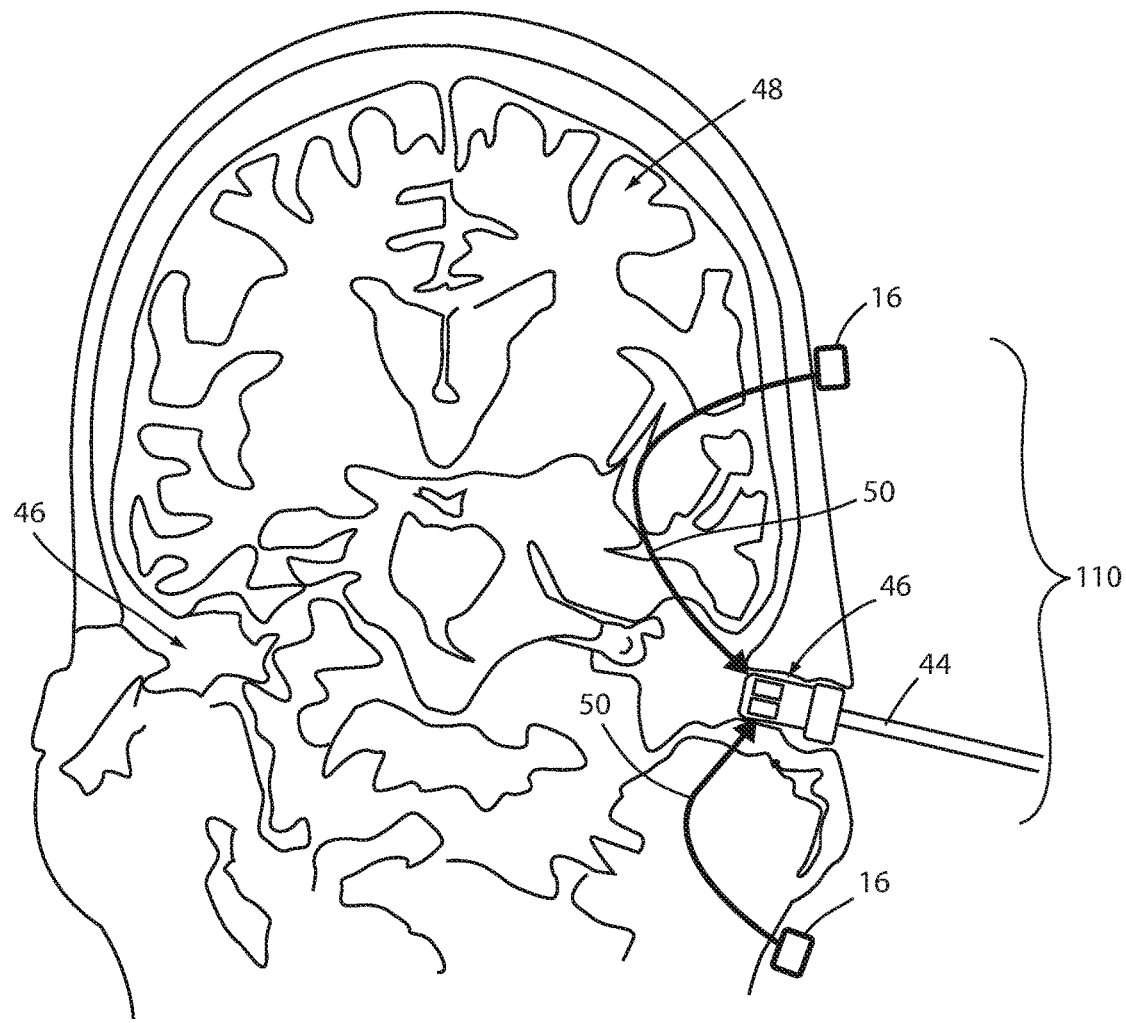
FIG. 6 is an elevation view of a subject's head showing the placement of components of a tissue monitoring system according to another embodiment.

An apparatus 110 according to a second embodiment of the present disclosure is shown in FIG. 6. Apparatus 110 includes a number of components that are the same as components of apparatus 10. Those common components are labeled with the same reference number and, unless otherwise explicitly stated below, operate in substantially the same manner as the like-numbered components of apparatus 10. Those components that are new to apparatus 110 are provided with a new reference number.

Apparatus 110 includes one or more light sources or emitters 16 and a probe 44. Probe 44 is adapted to be inserted into an orifice 46 of a subject's head 48. In the embodiment shown in FIG. 6, orifice 46 corresponds to the subject's ear canal. Generally speaking, apparatus 110 operates by having light sources 16 emit light toward the subject's brain and having light detectors 22 on probe 44 detect the emitted light that is scattered by the subject's brain tissue. FIG. 6 illustrates generalized light paths 50 that show an approximate path of some of the light that is emitted by emitters 16 and scattered by the subject's brain tissue in a manner that results in it being detected by the light detectors 22 of probe 44. A controller, such as microcontroller 24, is included as part of apparatus 110 and processes the outputs of the detected light in any of the manners discussed above.

Controller 24 is incorporated into probe 44 and communicates either by wire or wirelessly with emitter(s) 16, in some embodiments. In other embodiments, controller 24 is incorporated into one or more of the emitters 16 and communicates with probe 44 either by a wired or wireless connection. In still other embodiments, controller 24 is spaced from both emitters 16 and probe 44, but in communication with both of them via wired or wireless connections, or a combination of both wired and wireless connections.

Controller 24 synchronizes the emission of light by emitters 16 and the detection of the scattered light by light detectors 22. That is, controller 24 sends a signal to light emitters 16 controlling when the emitters 16 emit their light. At approximately the same time, controller 24 either sends a signal to light detectors 22 to start taking light detection readings, or starts recording such readings without the need for a separate signal. However implemented, controller 24 ensures that the readings from detectors 22 are taken at the time at least one emitter 16 is emitting light (or for a predetermined brief period of time after the emission of such light). This helps remove noise that may otherwise be detected by detectors 22 from extraneous sources during times when emitter 16 is not emitting light whose scattering is to be detected.

By positioning probe 44 inside of an orifice of the subject's head, it is possible to monitor tissues inside of the subject's brain that are deeper than what could otherwise be monitored if light detectors 22 were not positioned on probe 44, but instead were positioned on an exterior surface of the subject's head 48. This enables apparatus 110 to monitor portions of one or more of the following anatomical areas of the subject (which may vary depending upon the variations in the morphology of the subject): the subject's brain stem, cerebellum, deep gray structures, deep white matter, temporal lobes, inferior temporal gyrus, internal carotid artery, middle cerebral artery, and/or posterior cerebral artery. Further, if probe 44 is inserted into a different orifice 46 of the subject's head, such as a nasal passage or mouth, still other areas of the subject's head, neck, and/or brain may be monitored, including, but not limited to, various blood supplies to the neck and head of the subject.

Although FIG. 6 illustrates probe 44 as being physically separated from light source 16, it will be understood that apparatus 110 can be modified from the manner in which it is illustrated in FIG. 6. For example, in one embodiment, light source 16 is slidingly mounted to a rail, or other structure, that extends toward (and, in some cases, is coupled to), probe 44. The rail, or other device, includes structure for measuring an approximate distance between probe 44 and light source 16. This distance estimation is used by controller 24 for estimating a depth which the scattered light detected by detectors 22 has penetrated into the subject's head. In some embodiments, the structure includes measurement indicia that enable a user to visually determine the approximate distance between probe 44 and light source 16, in which case the user enters this information using a suitable user interface. In other embodiments, the structure automatically measures this distance and communicates it to controller 24. In still other embodiments, light source 16 is attached to a patch that is adhered to the subject's head and the patch is appropriately marked with one or more reference points for aligning the patch with respect to the user's ear canal at one or more predetermined distances. Still other variations are possible.

Light source 16 of apparatus 110 includes multiple light sources that emit light at different frequencies (i.e. light having different wavelengths). In one embodiment, light source 16 includes two light sources, one of which emits light at a frequency corresponding to a visible red color, and another of which emits light at frequency corresponding to a near infrared signal. In other embodiments, different frequencies may be used. Further, in some embodiments, more than two light sources may be used. Regardless of the number of light sources used, controller 24 is in communication with light source 16 so that controller 24 knows which light source is emitting light at which time, thereby enabling controller 24 to know the origin of the scattered light detected by light detector 22. Further, as discussed above, the original of the scattered light detected by light detector 22 is used by controller 24 to discern information about the subject's tissue due to the different levels at which different light frequencies are absorbed by different types of molecules within the subject's head (e.g. oxyhemoglobin and deoxyhemoglobin).

Although FIG. 6 and the accompanying discussion of apparatus 110 are based upon light sources 16 being positioned on the exterior of the subject's head and light detectors 22 being positioned on probe 44, it will be understood by those skilled in the art that this may be reversed. That is, apparatus 110 may be modified such that probe 44 includes one or more light sources 16 (which emit at least two different frequencies of light) and light detectors 22 are positioned along the exterior of the subject's head, such as in those positions of FIG. 6 where light sources 16 are shown.

FIGS. 7-10 illustrate in greater detail one embodiment of probe 44. Probe 44 includes a distal end 52 and a proximal end 54. Distal end 52 is inserted into the subject's orifice, such as, but not limited to, the subject's ear canal. Although not shown, proximal end 54 may be hollow to enable one or more electrical cords, wires, and/or air supply hoses to extend out of the inside of probe 44 and connect to a display, user interface, pressurized air source, and/or other device. In some embodiments, the wires or cords couple probe 44 to controller 24, which may be positioned within the display, user interface, or other device. Also, in some embodiments where probe 44 is intended to be inserted into the subject's nose or mouth, the air supply hoses can be provided to enable air to be delivered to the patient through the hose, as will be discussed in greater detail below.

Distal end 52 includes a first inflatable bladder 56 (FIGS. 7-10). One or more light detectors 22 are mounted generally around the circumference of first inflatable bladder 56. First inflatable bladder 56 is shown in a generally deflated state in FIGS. 7 & 8 and in an inflated state in FIGS. 9 & 10. First inflatable bladder 56 is selectively inflatable in order to position one or more of detectors 22 in contact with the interior surface of the subject's orifice. That is, after probe 44 is inserted into the subject's orifice, a source of pressurized air (not shown) is used to inflate bladder 56 such that at least one of detectors 22 contacts the interior surface of the subject's orifice. The pressurized air may come from any suitable external source and may be coupled to the first bladder 56 through suitable air tubing, which may extend through the hollow portion of proximal end 54. A pressure sensor may be included within first inflatable bladder and in communication with controller 24 to ensure a proper inflation level is achieved for first bladder 56. Prior to removal of probe 44, air may be allowed to escape from bladder 56 in order to allow probe 44 to be more easily removed from the subject's orifice.

Probe 44 also includes, in at least some embodiments, a second inflatable bladder 58. Second inflatable bladder 58 is positioned adjacent first bladder 56 on a side of first bladder 56 closer to proximal end 54 of probe 44. Second inflatable bladder 58 is constructed of a suitably opaque material that is adapted to prevent ambient light (including both visible and infrared light) from entering into the subject's orifice when second inflatable bladder 58 is inflated. Thus, after inserting probe 44 into the subject's orifice, second inflatable bladder 58 is inflated until its exterior comes into contact with the interior surface of the subject's orifice. This contact forms a seal that prevents ambient light from entering into the subject's orifice, thereby helping to ensure that the light detected by light detectors 22 is only that light which originated from light sources 16 and was scattered while passing through the subject's brain tissue.

Second inflatable bladder 58 may be coupled to the same source of pressurized air that first inflatable bladder 56 is coupled to. A user interface (not shown) that is coupled to the pressurized source of air allows the user of apparatus 110 to control the inflation and deflation of both first and second inflatable bladders 56 and 58. In those embodiments where probe 44 is intended to be inserted into the subject's nose or mouth, an air supply hose or passageway is included that passes through the interior of probe 44 and supplies air to the subject to enable him or her to continue to breath while second inflatable bladder 55 is inflated. The passageway is suitable designed to substantially prevent ambient light from entering into the interior of the nasal passage or mouth where detectors 22 are positioned.

In some embodiments, probe 44 also includes one or more sensors 60 adapted to allow the user to determine the position of probe 44 relative to the inside of the subject's orifice. That is, probe 44 includes, in some embodiments, one or more sensors 60 adapted to provide information to the user regarding how deeply probe 44 is positioned inside of the subject's orifice. In at least one embodiment, sensor 60 of probe 44 is an image sensor, such as a camera, that is connected to an external display that displays images captured by the image sensor. The camera is, in at least one embodiment, a video camera that continuously displays video images of the inside of the subject's orifice. In some of these video camera embodiments, a light may be included on the distal end 52 of probe 44 that is selectively illuminated in order to provide sufficient illumination for the video camera to capture video images. The light is controllable by a user such that it may be turned off during the capture of scattered photons emitted from light sources 16 (or alternatively is of a frequency that is either not detected by detectors 22 or one that can be filtered out from the signals detected by detectors 22).

In another embodiment, sensor 60 is a pressure sensor positioned at distal end 52 of probe 44 that is adapted to supply a signal to the user if/when probe 44 is inserted sufficiently far into the subject's orifice so as to cause contact between distal end 52 and one or more anatomical structures of the subject. For example, when probe 44 is inserted into a subject's ear canal, pressure sensor 60 is adapted to be triggered when it comes into contact with the subject's ear drum. Pressure sensor 60 therefore provides a signal to an external device (such as, but not limited to, a display) that indicates to a user when contact with the ear drum occurs. This signaling helps ensure that the user pushes probe 44 sufficiently far into the subject's orifice to monitor the deeper tissues of the subject's brain without causing damage to the subject's ear drum (or other internal anatomical structures).

Figure 11:
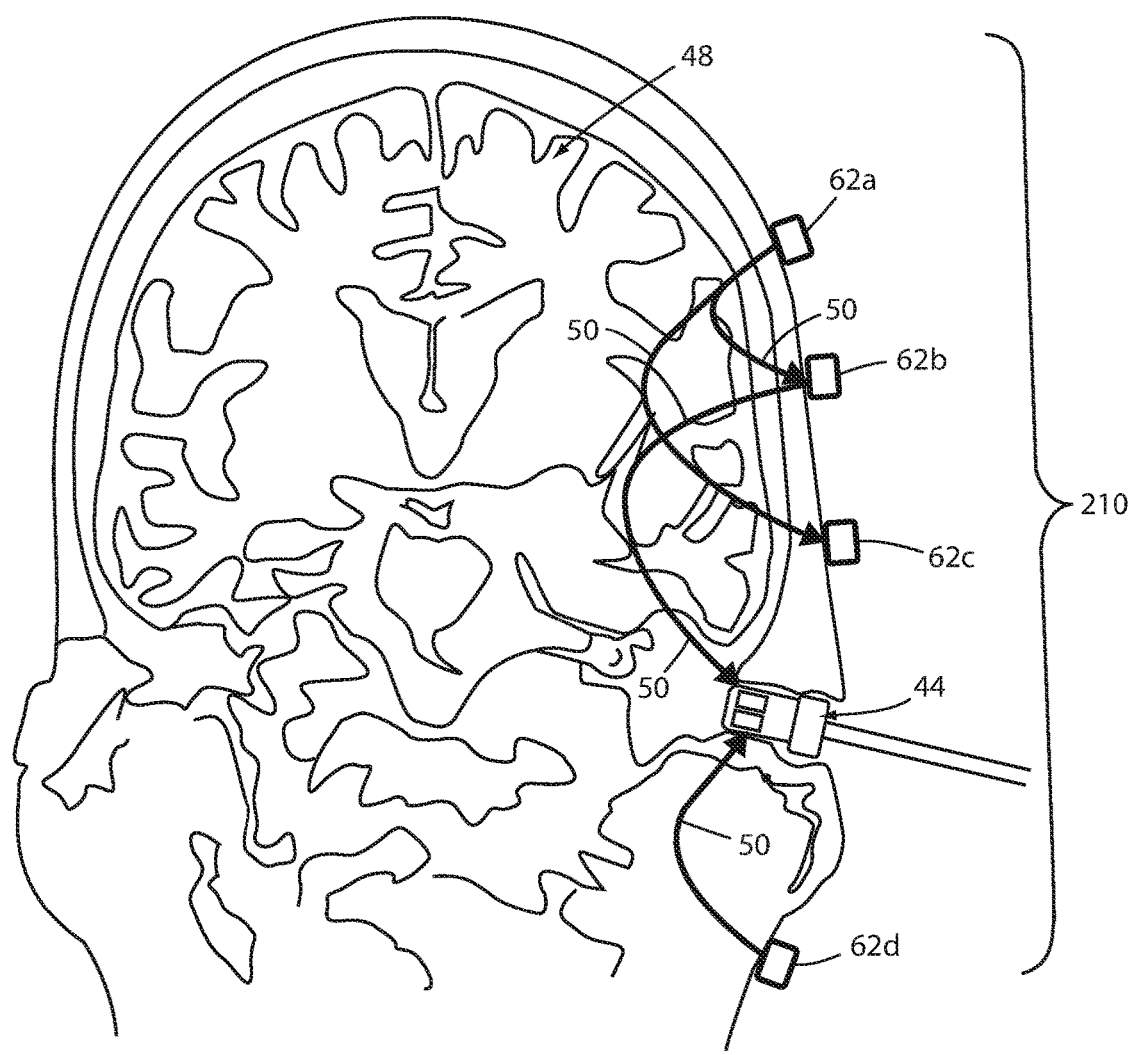
FIG. 11 is an elevation view of a subject's head showing the placement of a tissue monitoring system according to still another embodiment.

An apparatus 210 according to a second embodiment of the present disclosure is shown in FIG. 11. Apparatus 210 includes a number of components that are the same as components of apparatuses 10 and/or 110. Those common components are labeled with the same reference number and, unless otherwise explicitly stated below, operate in substantially the same manner as the like-numbered components of apparatuses 10 and/or 110. Those components that are new to apparatus 210 are provided with a new reference number.

Apparatus 210 includes a plurality of units 62 that are not present in apparatus 110. Units 62 each comprise a plurality of light emitters 16 and at least one light detector 22. A controller 24, not shown, is in communication with each unit 62 and synchronizes the activation of each light emitter 16 and each detector 22. When in use, controller 24 activates a first light source 16, such as one integrated into first unit 62*a* while also activating detectors 22 on each of the other units 62*b*, 62*c*, and/or 62*d* (as well as the detectors 22 incorporated into probe 44). After readings are gathered from each of the detectors, controller 24 activates another light source 16, such as the other light source on first unit 62*a* that has a different frequency, while continuing to activate one or more of the detectors 22 that are not part of the same unit 62 that contains the activated light source 16. After these readings from detectors 22 are gathered, controller 24 continues in a similar fashion by activating another light source 16 and simultaneously activating those detectors 22 that are not part of the same unit 62 as the activated light source 16. This process continues until all of the light sources 16 have been activated, including any light sources 16 that are present (in some embodiments) on probe 44.

In some embodiments of apparatus 210, all of units 62 are positioned on a patch, or other substrate, that is coupled to the patient's head. Further, in such embodiments, the units 62 are coupled to the patch or other structure at known relative distances to each other so that the distance between a light emitter 16 and each of the detectors 22 is known by controller 24. In at least one embodiment, the patch includes an aperture that is placed over the patient's ear canal, thereby allowing the user to insert probe 44 into the subject's ear canal. In such embodiments, the distance of each unit 62 and its corresponding light emitters from the aperture is known and stored in a memory accessible to controller 24 so that controller 24 can estimate the penetration depth of the scattered light detected by light detectors 22. In some embodiments, the memory also takes into account an estimated distance by which probe 44 is likely to be inserted into the subject's ear canal when computing the penetration depth of the detected scattered light.

Apparatus 210, by including units 62 in addition to probe 44, is able to provide greater tissue monitoring coverage than apparatus 110. That is, by including multiple units 62 that each have light sources 16 and detectors 22, it is possible to monitor the subject's brain tissue at both greater depths and over larger regions. Controller 24 processes the outputs from each of the detectors 22 and, coupled with information about which light emitter 16 emitted the detected light and the known distance between the light emitter 16 and the detectors 22, determines relative amounts of light absorption and/or scattering occurring over the subject's monitored head regions. This information is displayed in any suitable manner to the user, thereby providing the user with clinical data regarding the current state of the subject's brain tissues.

Apparatus 210 can be modified by including one or more units 62 that include only detector(s) 22 or only emitter(s) 16, instead of including both detector(s) 22 and emitter(s) 16 in the same unit 62. Alternatively, apparatus 210 can include a mix of units 62, some of which have both detector(s) 22 and emitter(s) 16 and some of which have only detector(s) 22 or emitter(s) 16.

Figure 12:
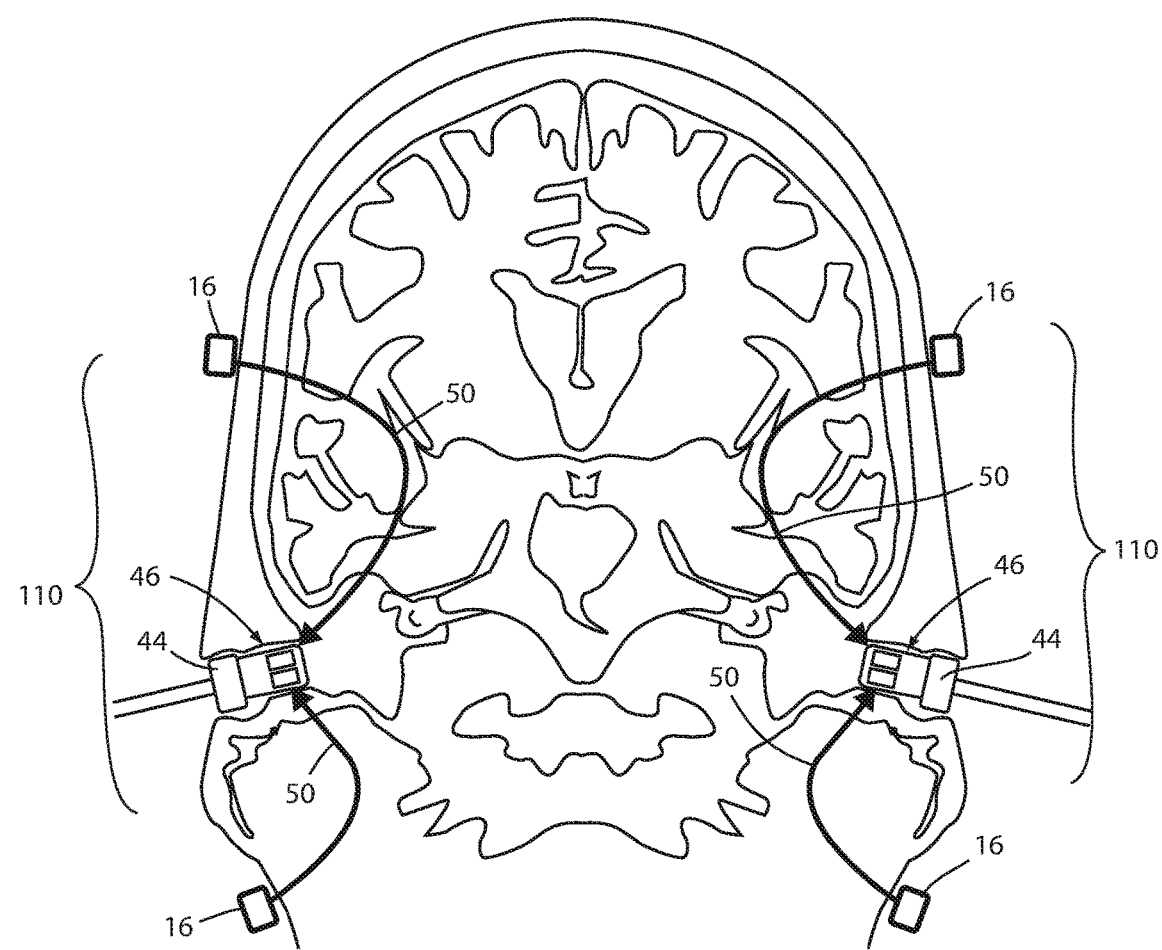
FIG. 12 is an elevation view of a subject's head showing the placement of a tissue monitoring system according to still another embodiment.

It will be understood that apparatus 110 and/or apparatus 210, or their modified versions, can be used as a pair wherein one apparatus 110, 210 is placed on the right side of the subject's head and another apparatus 110, 210 is placed on the left side of the subject's head (see, e.g. FIG. 12). When used in combination in this manner, controller 24 communicates with both sets of apparatuses 110 or 210. Further, controller 24 compares the data received from each apparatus and determines if differences of potential significance are detected between the two apparatuses, which may be indicative of a stroke, or other abnormality of the subject's brain. In some of these embodiments, the probes 44 and/or units 62 each include temperature sensors that detect temperatures of the subject's head and/or orifice 46 on opposite sides of the head. Controller 24 compares one or more of the temperature readings from the left side of the subject's head with one or more of the temperature readings from the right side of the subject's head and reports the temperature readings to the user. In some embodiments, if the temperature difference exceeds a threshold, controller 24 provides an indication to the user of the temperature difference. Temperature differences above a threshold between corresponding locations on or in the subject's head may be indicative that the subject has experienced, or is experiencing, a stroke.

In still another embodiment, apparatuses 110 and/or 210 are modified to include a first probe 44 that is inserted into the subject's right ear canal and a second probe 44 that is inserted into the subjects left ear canal. Further, in this embodiment, each probe 44 is modified to also include at least two light sources 16. Depending upon the particular anatomy of the subject's head, some of the light emitted from the first probe 44 positioned inside the subject's right ear canal is detected by the light detectors 22 coupled to the second probe 44 positioned inside the subjects left ear canal. Alternatively, or additionally, some of the light emitted from second probe 44 positioned inside of the subject's left ear canal is detected by the light detectors 22 coupled to the first probe 44 positioned inside the subject's right ear canal. By monitoring the amounts of light detected by detectors 22 of each probe 44, the state of the subject's brain tissue in regions between the ear canals can be monitored.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. An apparatus for monitoring a subject's tissue, the apparatus comprising:
a light emitter adapted to emit light through tissue in the subject's head;
a light detector adapted to detect light emitted from the light emitter and scattered by the tissue of the subject's head;
a probe adapted to be inserted into an orifice of the subject's head, the probe including the light detector, and the light emitter being adjustably positionable with respect to the probe such that the light emitter may be placed at different locations on the subject's head while the probe remains in the subject's orifice; and
a controller in communication with the light detector and light emitter and adapted to detect an oxygenation level of blood in the subject's head based upon measurements of the scattered light detected by the light detector.

2. The apparatus of claim 1 wherein the subject's orifice is an ear canal.

3. The apparatus of claim 2 wherein the probe further includes a temperature sensor.

4. The apparatus of claim 1 wherein the first light emitter emits light having a first wavelength and the second light emitter emits light having a second wavelength, the first and second wavelengths being different.

5. The apparatus of claim 4 wherein the first wavelength corresponds to a red light and the second wavelength corresponds to an infrared light.

6. The apparatus of claim 4 wherein the probe further includes a first inflatable bladder adapted to urge the light detector against an interior surface of the orifice when the first inflatable bladder is inflated.

7. The apparatus of claim 6 further comprising a second inflatable bladder coupled to the probe, the second inflatable bladder adapted to inflate inside of the subject's orifice and block ambient light from reaching the light detector.

8. The apparatus of claim 7 further comprising a sensor for determining a relative location of the probe within the orifice.

9. The apparatus of claim 8 wherein the sensor is a pressure sensor.

10. An apparatus for monitoring a subject's tissue, the apparatus comprising:
a first unit having first and second light emitters adapted to emit light through a first region of the subject's head while the first and second light emitters are positioned outside of the subject's first and second ear canals;
a second unit having third and fourth light emitters adapted to emit light though a second region of the subject's head while the third and fourth light emitters are positioned outside of the subject's first and second ear canals;
a first probe adapted to be inserted into the first ear canal of the subject, the first probe including a first light detector, a first temperature sensor, a first inflatable bladder, and a second inflatable bladder, the first light detector adapted to detect light emitted from the first and second light emitters and scattered by the first region of the subject's head, the first inflatable bladder adapted to urge the first light detector against an interior surface of the first ear canal when the first inflatable bladder is inflated, and the second inflatable bladder adapted to inflate inside the first ear canal and block ambient light from reaching the first light detector;
a second probe adapted to be inserted into the second ear canal of the subject, the second probe including a second light detector adapted to detect light emitted from the third and fourth light emitters and scattered by the second region of the subject's head, the second probe also including a second temperature sensor; and
a controller in communication with the first and second light detectors and adapted to detect an oxygenation level of blood in the first region of the subject's head based upon measurements of the scattered light detected by the first light detector, to detect an oxygenation level of blood in the second region of the subject's head based upon measurements of the scattered light detected by the second light detector, and to compare temperature readings from the first and second temperature sensors.

11. The apparatus of claim 10 wherein the first probe further comprises a pressure sensor adapted to facilitate determining a relative location of the first probe within the first ear canal.

\* \* \* \* \*